United States Patent [19]

Nelson

[11] 4,323,558
[45] Apr. 6, 1982

[54] TOPICAL TRIEN CONTAINING PHARMACEUTICAL COMPOSITIONS AND METHODS OF USE

[75] Inventor: Eric L. Nelson, Santa Ana, Calif.

[73] Assignee: Nelson Research & Development Co., Irvine, Calif.

[21] Appl. No.: 176,076

[22] Filed: Aug. 7, 1980

Related U.S. Application Data

[63] Continuation-in-part of Ser. No. 73,932, Sep. 10, 1979, abandoned.

[51] Int. Cl.$^3$ ...................... A61K 33/04; A61K 31/13
[52] U.S. Cl. .................................... 424/164; 424/233; 424/240; 424/245; 424/253; 424/260; 424/274; 424/324; 424/325; 424/338; 424/355
[58] Field of Search ............................... 424/325, 164

[56] References Cited

PUBLICATIONS

Chemical Abstracts 66:26796b (1967).
Chemical Abstracts 80:293z (1974).

Primary Examiner—Leonard Schenkman
Attorney, Agent, or Firm—Martin A. Voet

[57] ABSTRACT

Pharmaceutical compositions containing triethylenetetramine (trien) useful in treating skin disorders. Trien may be used alone to treat inflammation of the skin or may be combined with additional anti-inflammatory, anti-infective or antimitotic agents in the treatment of skin disorders such as acne, psoriasis, seborrhea and dermatitis. Trien also forms a clear solution or gel with zinc pyrithione.

16 Claims, No Drawings

TOPICAL TRIEN CONTAINING PHARMACEUTICAL COMPOSITIONS AND METHODS OF USE

REFERENCE TO EARLIER FILED APPLICATION

This application is a continuation-in-part of U.S. Ser. No. 073,932 filed Sept. 10, 1979 now abandoned.

BACKGROUND OF THE INVENTION

1. Field of the Invention

The invention relates to pharmaceutical compositions and methods for their use. More particularly the invention relates to topical compositions containing triethylenetetramine useful in treating skin disorders.

2. Background of the Prior Art

Triethylenetetramine (trien) is known to be a copper chelating agent and has been used heretofore therapeutically in the treatment of Wilson's Disease, a degenerative liver condition characterized by excessive levels of copper in the body. (Walshe, J. M. Lancet, 1969, ii, 1401; 1970, 154; 1972, 853.) The treatment described for Wilson's Disease consists of oral dosages of 400 mg capsules of trien in the amount of three or four capsules daily (1.2 or 1.6 grams daily).

Psoriasis is a common, relapsing inflammatory disease of unknown etiology which consists of elevated, silvery dry lesions which are known as plaques. Pathologically, there are three obvious changes associated with the disease: (1) increase in the rate of cell division of the epidermis, (2) striking increase in the thickness of the cornified epithelium, and (3) proliferation of the subepithelial capillaries.

Current therapy consists mostly of topical antimitotic agents containing active ingredients such as coal tars or steroids. Ultraviolet radiation has also been used. Occasionally, psoriasis is such a serious problem that systemic antimetabolites are employed to control epithelial proliferation, e.g., U.S. Pat. No. 3,749,784.

Acne is a common epidermal disorder affecting humans, characterized by a frequently pustular eruption of the skin, especially the face. In addition to the unsightly appearance caused by acne, severe acne cases with infected skin eruptions may result in permanent facial scars.

Zinc pyrithione is a commercially available antimicrobial compound (known commercially as Zinc Omadine) and is used commercially in the treatment of dandruff by combining it with shampoo. A problem with zinc pyrithione is that it is very insoluble and must be used in the form of cloudy suspensions. It would be advantageous if zinc pyrithione could be formulated as a clear solution or gel so that it could be made into pharmaceutically elegant formulations.

SUMMARY OF THE INVENTION

It has now been discovered that trien may be used topically in the treatment of inflammation in humans and animals. While the precise mechanism of action of trien is not known, it is believed that the topical anti-inflammatory activity of trien results from the action of trien in inhibiting leucocite migration.

In addition, it has been discovered that trien, in combination with a conventional anti-infective agent, is effective in the topical treatment of skin conditions such as acne, fungal infections and as a deodorant.

In addition, it has been discovered that trien, in combination with conventional anti-inflammatory and antimitotic agents, is effective in the topical treatment of skin conditions such as psoriasis and seborrhea.

It has also been discovered that when trien is combined with zinc pyrithione, a clear solution results which is pharmaceutically elegant and has unexpected and improved substantivity when applied topically to the skin, making the formulation especially useful in the treatment of acne and fungal infections.

DESCRIPTION OF THE INVENTION

Triethylenetetramine (trien) is commercially available as a technical grade reagent which must be purified prior to use by methods known in the art, for example, as disclosed in Lancet, 1970, ii, 775 (Dubois et al); and Lancet, 1972, 853 (Dixon et al). The amount of trien which may be used in the present invention ranges from about 1 to about 25 and preferably about 5 to about 20 percent by weight. The preferred form of trien is the free base.

Zinc pyrithione is commercially available in a pharmaceutical grade (Olin Chemicals Zinc Omadine). The amount of zinc pyrithione which may be used in the present invention ranges from about 0.01 to about 5 and preferably about 0.1 to about 2 percent by weight.

The preferred manner of administration is topical, that is, local administration of solutions, gels, lotions and the like to the affected skin, including intralesional injection.

Conventional, pharmaceutically acceptable carriers include conventional emulsifiers, such as fatty alcohols, glycol ethers and esters of fatty acids; conventional emollients, such as isopropyl and butyl esters of fatty acids, e.g., isopropyl myristate, glycerin, propylene glycol and alcohols; oils such as mineral oil, petroleum oil, oil extracts from animal or vegetable sources; conventional stabilizers including antioxidants and preservatives. The formulation may also include agents, such as urea, to improve the hydration of the skin. In addition to the foregoing conventional formulations, the solubility of the trien formulations may be improved with the use of compounds which aid solubility, such as 2-pyrrolidone and N-lower alkyl-2-pyrrolidones, such as N-methyl-2-pyrrolidone and 1-substituted azacycloalkan-2-ones such as, for example, 1-n-dodecylazacycloheptan-2-one and other compounds disclosed in U.S. Pat. No. 3,989,816. The amount of these compounds which may be used in the present invention ranges from about 0.1 to 25 percent and preferably about 1 to 15 percent by weight of the composition.

The amount of the composition to be administered will obviously be an effective amount for the desired result expected therefrom. This, of course, will be ascertained by the ordinary skill of the practitioner. In accordance with the usual prudent formulating practices, a dosage near the lower end of the useful range of the particular agent may be employed initially and the dosage increased as indicated from the observed response, as in the routine procedure of the physician.

In carrying out the novel method employing the topical route, the active ingredient(s) formulated, for example, as an ointment or solution is applied to the affected area of the skin at a rate varying from 0.2 mg per square cm of skin surface per day up to 10 mg per square cm of skin surface per day until the appearance of the affected skin has returned to normal. The ointment or solution is generally applied for several days, and in the case of psoriasis, preferably using a continuous occlusive dressing. The concentration of active ingredients can vary from about 0.1% to about 10% by weight. With the foregoing concentration, a dose of 0.2 ml per square cm of skin surface readily supplies the amount of active ingredient specified above.

Suitable anti-infective agents which may be used in the invention include conventional anti-infective agents including antimicrobial agents, antibacterial agents and antifungal agents.

Typical antibacterial agents which may be used in this invention include sulfonomides, penicillins, cephalosporins, penicillinase, erythromycins, lincomycins, vancomycins, tetracyclines, chloramphenicols, streptomycins, etc. Typical examples of the foregoing include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracycline, minocycline, etc., and benzoyl peroxide and fusidic acid, including pharmaceutically acceptable salts thereof, e.g. sodium fusidate in amounts ranging between about 0.1 and about 15% by weight.

Fungistatic and fungicidal agents such as, for example, thiabendazole, chloroxine, amphotericin, candicidin, fungimycin, nystatin, chlordantoin, clotrimazole, ethonam nitrate, miconazole nitrate, pyrrolnitrin, salicylic acid, fezatione, ticlatone, tolnaftate, triacetin and zinc and sodium pyrithione may be used in the compositions described herein and topically applied to affected areas of the skin. The subject composition may also be employed in the treatment of fungus infections on the skin caused by candida and dermatophytes which cause athletes foot or ringworm, by applying thiabendazole or similar antifungal agents in the composition as described and applying it to the affected area.

Suitable antimitotic agents (or cytostatic agents) such as zinc pyrithione which may be used in the invention include selenium sulfide, coal tar, colchicine and phosphodiesterase inhibitors, such as, theophylline and papaverine and certain cyclic nucleotide analogues.

Suitable anti-inflammatory agents which may be used in the invention include conventional anti-inflammatory agents such as steroids, salicylates and indomethacin.

The foregoing anti-infective agents, antimitotic agents and anti-inflammatory agents are used herein in conventional amounts.

Skin conditions such as psoriasis may be treated by topical application of a solution of a conventional topical steroid in one of the subject formulations or by treatment with theophylline or antagonists of β-adrenergic blockers such as isoproterenol in one of the vehicles. Scalp conditions such as alopecia areata may be treated more effectively by applying steroids such as triamcinolone acetonide combined in one of the subject formulations of this invention directly to the scalp.

The subject compositions are also useful for treating mild eczema, for example, by applying a solution of fluocinolone acetonide or its derivatives; hydrocortisone, triamcinolone acetonide, indomethacin, or phenylbutazone dissolved in one of the formulations to the affected area.

Examples of other physiologically active steroids which may be used with the vehicles include corticosteroids such as, for example, cortisone, cortodoxone, flucetonide, fludrocortisone, difluorsone diacetate, flurandrenolone acetonide, medrysone, amcinafel, amcinafide, betamethasone and its esters, chloroprednisone, clocortelone, descinolone, desonide, dexamethasone, dichlorisone, difluprednate, flucloronide, flumethasone flunisolide, fluocinonide, flucortolone, fluoromethalone, fluperolone, flupredisolone, meprednisone, methylmeprednisolone, paramethasone, prednisolone and prednisone.

Combinations of trien and zinc pyrithione may be used in the therapeutic treatment of acne, seborrhea and athelete's foot and have been found to have great substantivity. That is, the antimicrobial activity is taken up by the skin and remains there for long periods.

Amounts of the foregoing conventional anti-infective, antimitotic and anti-inflammatory agents which may be used in this invention are conventional amounts used topically.

EXAMPLE I

The formulation shown below was prepared by either of the methods indicated below:

| Ingredients | % (By Wt.) |
| --- | --- |
| Trien (free base) | 5.0 |
| Zinc Pyrithione | 1.0 |
| N-Methyl-2-Pyrrolidone | 10.0 |
| 2-Propanol | to 100.0 |

1. The trien was dissolved in the N-methyl-2-pyrrolidone and combined with ¼ of the 2-propanol. To this mixture was added the zinc pyrithione and the resulting mixture was stirred for about 20 minutes (until all of the zinc pyrithione was dissolved) and the remaining 2-propanol was then combined to form a clear solution. 2. The trien was dissolved in the N-methyl-2-pyrrolidone and combined with all of the 2-propanol. To this mixture is added the zinc pyrithion which was stirred until the zinc pyrithion became dissolved (60 to 90 minutes) to form a clear solution.

EXAMPLE II

The following formulations are prepared according to the method of Example I.

| Ingredient | % (by weight) | | | | | | | |
| --- | --- | --- | --- | --- | --- | --- | --- | --- |
| | A | B | C | D | E | F | G | H |
| Trien (free base) | 1 | 3 | 3 | 5 | 5 | 8 | 8 | 10 |
| Zinc Pyrithione | — | — | 0.2 | — | — | — | — | — |
| Selenium Sulfide | 0.5 | — | — | — | — | — | — | — |
| Coal Tar | — | 1.0 | — | — | — | — | — | — |
| Benzoyl Peroxide | — | — | 2.0 | — | — | — | — | — |
| Fusidic Acid | — | — | — | 1.0 | — | — | — | — |
| Indomethacin | — | — | — | — | 1.0 | — | — | — |
| Clindamycin | — | — | — | — | — | 1.0 | — | — |
| Thiabendazole | — | — | — | — | — | — | 1.0 | — |
| Salicylic Acid | — | — | — | — | — | — | — | 2.0 |
| N-Methyl-2-Pyrrolidone | 10 | 10 | 10 | 10 | 10 | 10 | 10 | 10 |
| 2-Proponol to | 100 | 100 | 100 | 100 | 100 | 100 | 100 | 100 |

EXAMPLE III

The following formulations are suitable for use in the treatment of inflammation and especially acne.

| Ingredient | % (by weight) | | | | | |
|---|---|---|---|---|---|---|
| | A | B | C | D | E | F |
| Sodium Fusidate | 1 | 1 | 1 | — | — | — |
| Trien (33% overage) | 15 | 15 | 15 | 15 | 0.3 | 15 |
| Azone* | 1 | — | 1 | 1 | 1 | 1 |
| 2-Proponol | 46.5 | — | — | 46.5 | 49.3 | 46.5 |
| Water | 36.5 | 39 | 32 | 36.5 | 49.3 | — |
| Carbopol 940 | — | — | 50 | — | — | 36.5 |
| Clindamycin | — | — | — | 1 | — | 1 |
| Triethanolamine | — | — | 1 | — | — | — |
| Zinc Omadine | — | — | — | — | 0.1 | — |
| N-Methyl-2-Pyrrolidone | — | 10 | — | — | — | — |
| Beeswax | — | 1 | — | — | — | — |
| Solulan 97 | — | 4 | — | — | — | — |
| Solulan L575 | — | 4 | — | — | — | — |
| Tween 20 | — | 3 | — | — | — | — |

*Azone - Trademark for 1-n-dodecylazacycloheptan-2-one.

EXAMPLE IV

Formulation B of Example III was tested with three acne patients for eight weeks with the formulation being applied in conventional amounts topically on a twice daily basis. The results were rated by a clinician as follows:

| Patient | Good | Improved | No Effect |
|---|---|---|---|
| 1 | X | | |
| 2 | | X | |
| 3 | | X | |

EXAMPLE V

Formulation B of Example III was tested in three patients against a herpes simplex inflammation with the formulation being applied in conventional amounts topically. Withing 12 hours, the redness or soreness cleared in each patient.

EXAMPLE VI

Formulation B of Example III was tested in a patient having a minor infected skin wound with accompanying diffuse redness and swelling. Within six hours of a topical application, the redness was significantly reduced and healing commenced within 24 hours.

EXAMPLE VII

Formulation B of Example III was tested in four patients having facial blemishes and one patient having a chronic, red, weeping, inflamed facial lesion. After topical application, the redness associated with the blemishes in the four patients cleared in 12 hours; and the lesion showed significantly reduced symptoms of inflammation after two days topical treatment.

EXAMPLE VIII

Five separate clindamycin resistant strains of P. acnes were isolated from acne patients treated topically with clindamycin and used in a test of Formulation B of Example III. The results indicated that all of the strains of P. acnes were sensitive to Formulation B, having zones of inhibition ranging from 13–19 mm radius of inhibition in a standardized sensitivity test.

I claim:

1. A therapeutic composition limited to topical Application to the body comprising an effective anti-inflammatory amount of trien and a pharmaceutically acceptable topical carrier selected from the group consisting of gels, ointments and lotions.

2. The composition of claim 1 wherein an effective amount of trien is about 1 to about 25 percent by weight.

3. The composition of claim 1 additionally comprising an effective antimicrobial amount of fusidic acid or a pharmaceutically acceptable salt thereof.

4. The composition of claim 1 additionally comprising an effective, antimicrobial amount of an antimicrobial agent selected from the group consisting of an antibiotic agent and an antifungal agent.

5. The composition of claim 4 wherein the antimicrobial agent is zinc pyrithione.

6. The composition of claim 5 in a form a clear gel.

7. The composition of claim 1 additionally comprising an effective antimicrobial amount of sodium fusidate and an effective, penetration enhancing amount of a penetration enhancing vehicle.

8. The composition of claim 7 wherein the vehicle is selected from the group consisting of N-methyl-2-pyrrolidone and 1-n-dodecylazacycloheptan-2-one.

9. A therapeutic composition limited to topical application to the body comprising about 15% trien and about 1% sodium fusidate in a pharmaceutically acceptable topical carrier selected from the group consisting of gels, ointments and lotions.

10. The composition of claim 9 additionally containing about 10% N-methyl-2-pyrrolidone.

11. The composition of claim 9 additionally containing about 1% 1-n-dodecylazacycloheptan-2-one.

12. A method for topical treatment of inflammatory skin conditions comprising administering topically to the effected skin a therapeutically effective amount of a composition comprising an effective, anti-inflammatory amount of trien and a pharmaceutically acceptable carrier.

13. The method of claim 12 wherein the skin condition is acne and the composition additionally comprises an amount effective for treating acne of a compound selected from the group consisting of zinc pyrithione, benzoyl peroxide, fusidic acid and pharmaceutically acceptable salts thereof.

14. The method of claim 12 wherein the skin condition is psoriasis or seborrhea and the composition additionally comprises an amount effective for treating psoriasis or seborrhea of a member selected from the group consisting of zinc pyrithione, selenium sulfide, coal tar, colchicine, theophylline and papaverine.

15. The method of claim 12 wherein the skin condition is inflammation and the composition additionally comprises an amount effective for treating inflammation of a compound selected from the group consisting of a therapeutically useful steroid, a salicylate and indomethacin.

16. The method of claim 12 wherein the skin condition is associated with a microbial infection and the composition additionally comprises an effective, antimicrobial amount of an antimicrobial agent selected from the group consisting of an antibiotic agent and an antifungal agent.

* * * * *